(12) United States Patent
Dias (10) Patent No.: US 9,539,984 B2
(45) Date of Patent: Jan. 10, 2017

(54) METHOD AND DEVICE TO ASSESS THE WEAR OF A WINDSHIELD WIPER UNIT

(75) Inventor: Dominique Dias, St. Remy les chevreuses (FR)

(73) Assignee: Valeo Systèmes d'Essuyage, Le Mesnil Saint Denis (FR)

( * ) Notice: Subject to any disclaimer, the term of this patent is extended or adjusted under 35 U.S.C. 154(b) by 643 days.

(21) Appl. No.: 14/118,750

(22) PCT Filed: May 15, 2012

(86) PCT No.: PCT/EP2012/059069
§ 371 (c)(1),
(2), (4) Date: Nov. 19, 2013

(87) PCT Pub. No.: WO2012/159943
PCT Pub. Date: Nov. 29, 2012

(65) Prior Publication Data
US 2014/0088886 A1   Mar. 27, 2014

(51) Int. Cl.
*B60S 1/08* (2006.01)
*G01M 5/00* (2006.01)
*G01N 19/02* (2006.01)
*H02P 3/02* (2006.01)

(52) U.S. Cl.
CPC ............ *B60S 1/0818* (2013.01); *B60S 1/0859* (2013.01); *G01M 5/0033* (2013.01); *G01N 19/02* (2013.01); *H02P 3/02* (2013.01)

(58) Field of Classification Search
CPC ... B60S 1/0818; B60S 1/0859; G01M 5/0033; G01N 19/02; H02P 3/02
USPC ................. 702/34; 318/476, 432; 15/250.12
See application file for complete search history.

(56) References Cited

U.S. PATENT DOCUMENTS

| | | | | |
|---|---|---|---|---|
| 3,643,415 A | * | 2/1972 | Mackie ................. | D01H 7/26 57/117 |
| 4,265,157 A | * | 5/1981 | Fricke ................. | G10H 5/005 84/695 |
| 4,499,410 A | * | 2/1985 | Iacoponi ............. | B60S 1/08 15/DIG. 15 |

(Continued)

FOREIGN PATENT DOCUMENTS

| | | |
|---|---|---|
| DE | 25 04 799 A1 | 8/1976 |
| DE | 199 55 874 A1 | 5/2001 |
| EP | 1 010 594 A1 | 6/2000 |

OTHER PUBLICATIONS

International Search Report for corresponding International Application No. PCT/EP2012/059069, mailed Jul. 12, 2012 (2 pages).

*Primary Examiner* — Carol S Tsai
(74) *Attorney, Agent, or Firm* — Osha Liang LLP (57) ABSTRACT

Method to estimate the wear state of wiper blades (5) of a vehicle windshield wiper unit (1), said windshield wiper unit (1) comprising: at least one wiper blade (5) configured to wipe a windshield surface (S) when activated, at least one motor (7) configured to activate the at least one wiper blade (5), a controller (9) configured to control the at least one motor (7), comprising the steps: deriving a friction coefficient (B) between the at least one wiper blade (5) and the windshield surface (S), using the derived friction coefficient (B) to determine the wetness of the windshield surface (S), if the windshield surface (S) is dry, using the derived friction coefficient (B) to estimate the wear state of the at least one wiper blade (5).

16 Claims, 4 Drawing Sheets

(56) References Cited

U.S. PATENT DOCUMENTS

| | | | | |
|---|---|---|---|---|
| 4,733,142 A * | 3/1988 | Bicknell | B60S 1/0807 | 15/DIG. 15 |
| 5,119,002 A * | 6/1992 | Kato | B60S 1/0818 | 318/444 |
| 5,235,260 A * | 8/1993 | Furukoshi | B60S 1/08 | 318/443 |
| 5,285,138 A * | 2/1994 | Okada | B60S 1/0807 | 15/250.12 |
| 5,568,026 A * | 10/1996 | Welch | B60S 1/0814 | 318/41 |
| 5,860,185 A * | 1/1999 | Ponziani | B60S 1/08 | 15/250.13 |
| 6,144,906 A * | 11/2000 | Buchanan, Jr. | B60S 1/0807 | 307/9.1 |
| 6,679,579 B1 * | 1/2004 | Tee | B41J 2/16538 | 347/33 |
| 6,703,804 B1 * | 3/2004 | Courdier | B60S 1/08 | 318/280 |
| 6,917,173 B2 * | 7/2005 | Takagi | H02P 7/291 | 318/280 |
| 7,973,507 B2 * | 7/2011 | Yoshigoe | B60S 1/0818 | 318/466 |
| 8,303,079 B2 * | 11/2012 | Frazier | B41J 2/16535 | 347/33 |
| 2003/0087767 A1 * | 5/2003 | Goto | B60S 1/38 | 508/113 |
| 2008/0016644 A1 * | 1/2008 | Mizote | B60S 1/38 | 15/250.361 |
| 2008/0060677 A1 * | 3/2008 | Nakano | B60S 1/486 | 134/6 |
| 2008/0136361 A1 * | 6/2008 | Yoshigoe | B60S 1/0818 | 318/483 |
| 2010/0033532 A1 * | 2/2010 | Frazier | B41J 2/17593 | 347/33 |
| 2012/0301197 A1 * | 11/2012 | Ziegelmuller | G03G 21/0017 | 399/350 |

* cited by examiner

METHOD AND DEVICE TO ASSESS THE WEAR OF A WINDSHIELD WIPER UNIT

The invention relates to a method and a device to assess the wear state of a windshield wiper unit.

Replacement of wiper blades is based on driver balance between their comfort of well seeing in rainy condition, and the cost of replacement of the blades. Maintaining blades, as far as visibility is largely impacted, could bring the driver to a degraded vision in rainy condition, and increases the risk of accident due to loss of visibility.

A known solution to detect the wear state of wiper blades is to count the number of wiping cycle the blades achieved and to inform the user when a predetermined lifetime limit representative of a unacceptable wear state is reached. However, this method is not adapted to precisely account for the environmental factors such as exposure to ultra violet light, temperature and meteorological conditions.

Another known solution is to monitor the tear and wear of the wiper blade with an optical wetness sensor, with which the windshield is scanned before and after wiping operation. However, the optical wetness sensor can only monitor a fraction of the windshield. Hence data can only be gathered on a small part of the wiper blade, which results in an unreliable wear state assessment.

Another known solution is to fix a wear element made from the same material as the wiper blade to the supporting structure of the wiper blade. The wear element is subjected to the same operating and environmental condition as the wiper blade. At the end of the predetermined period of effectiveness, a section of the wear element breaks in order to reveal indication means that inform the users they should change their wiper blades. However, this method necessitates fabricating specific hardware. This fabrication process is usually complex.

It is accordingly an object of the invention to provide a method and a device to estimate the wear of the wiper blades of windshield wiper unit, which overcome the above-mentioned disadvantages of the heretofore-known methods and devices. The method of the invention gives accurate results that account for the wear state of the totality of the wiper blade and does not require adding complex hardware.

In order to overcome the aforementioned drawbacks, the invention has for object a method to estimate the wear state of wiper blades of a vehicle windshield wiper unit, said windshield wiper unit 1 comprising:
  at least one wiper blade configured to wipe a windshield surface when activated,
  at least one motor configured to activate the at least one wiper blade at a wiping speed,
  a controller configured to control the at least one motor,
said method comprises the steps:
  deriving a friction coefficient between the at least one wiper blade and the windshield surface,
  comparing the derived friction coefficient to a first predetermined threshold value, to determine the wetness of the windshield surface,
  if the windshield surface is dry, comparing the derived friction coefficient to a second predetermined threshold value in order estimate the wear state of the at least one wiper blade.

The invention provides a simple method to accurately monitor the wear of wiper blades of windshield wiper unit.

The method may have one or more of the following characteristics taken separately or in combination.

The at least one motor has a power consumption, and the method comprises a step of dividing the power consumption by a size factor of the windshield wiping unit.

The method comprises a step of dividing the derived friction coefficient by the size factor of the windshield wiping unit.

The windshield wiping unit wipes the windshield surface at a wipe angle and comprises at least one wiper arm, and at least one wiper blade, wherein said windshield wiping unit presents a size factor comprising the wipe angle, the length of the at least one wiper arm and the length of the at least one wiper blade.

The method comprises a step of determining the first predetermined threshold value with a test windshield wiping unit, said determination comprises the steps:
  wetting the test windshield surface,
  measuring the power consumption of the at least one test motor,
  determining the wiping speed of the at least one test wiper blade,
  using the measured power consumption and wiping speed to deduce a reference wet friction coefficient of the wet windshield surface,
  using the reference wet friction coefficient to determine the first predetermined threshold value.
  said determination comprises a step of dividing the power consumption or the first predetermined threshold value by the size factor of the test wiper unit.

The method comprises a step of determining the second predetermined threshold value with the test windshield wiping unit,
said determination comprises the steps:
  measuring the power consumption of the at least one test motor on dry test windshield surface,
  determining the wiping speed of the at least one test wiper blade on dry test windshield surface,
  using the measured power consumption and determined wiping speed to derive the friction coefficient,
  monitoring the over time wiping performance and the corresponding friction coefficient to determine the second predetermined threshold value,
said determination comprises a step of dividing the power consumption or the friction coefficient by the size factor of the test wiping unit.

The controller is connected to a windshield washing unit, the first predetermined threshold value is determined using a calibration, the calibration comprising the steps:
  wetting the windshield surface by activating the windshield washing unit,
  measuring the power consumption of the at least one motor during a certain number of cycles done by the at least one wiper blade,
  using the measured power consumption to deduce a reference wet friction coefficient of the wet windshield surface,
  using the reference wet friction coefficient to determine the first predetermined threshold value.

The first predetermined threshold value is a multiple of the reference wet friction coefficient, preferentially the first predetermined threshold value is at least four times the reference wet friction coefficient.

The second predetermined threshold value, is determined using a calibration, the calibration comprising the steps:
  measuring the power consumption of the at least one motor on dry windshield surface,
  determining the wiping speed of the at least one wiper blade on dry windshield surface, using the measured power consumption and determined wiping speed to derive an initial dry friction coefficient of the dry windshield surface, using said initial dry friction coefficient to determine the second predetermined threshold value.

The second predetermined threshold value is a multiple of the corresponding friction coefficient or the initial dry friction coefficient.

The method comprises a step of generating an alert signal when the at least one wiper blade is estimated worn.

The method comprises a step of storing the derived friction coefficient values and restoring them.

Also, the invention relates to the associates windshield wiper unit comprising:

at least one wiper blade configured to wipe a windshield surface when activated, at least one motor configured to activate the at least one wiper blade, a controller, configured to control the at least one motor, wherein the controller is configured to:

derive a friction coefficient between the at least one wiper blade and the windshield surface, compare the derived friction coefficient to a first predetermined threshold value, to determine the wetness of the windshield surface, if the windshield surface is dry, compare the derived friction coefficient to a second predetermined threshold value, in order to estimate the wear state of the at least one wiper blade.

The controller comprises means for performing a calibration of the first predetermined threshold value and of the second predetermined threshold value.

The controller comprises means to generate an alert signal when the at least one wiper blade is estimated worn.

The controller comprises means for storing the values of the derived friction coefficient and restoring them.

The invention main advantage is to provide a simple method and device to accurately monitor the wear of wiper blades of windshield wiping unit.

Other characteristics and advantages will appear at the reading of the following description of the accompanying figures, among which.

Figure 1:
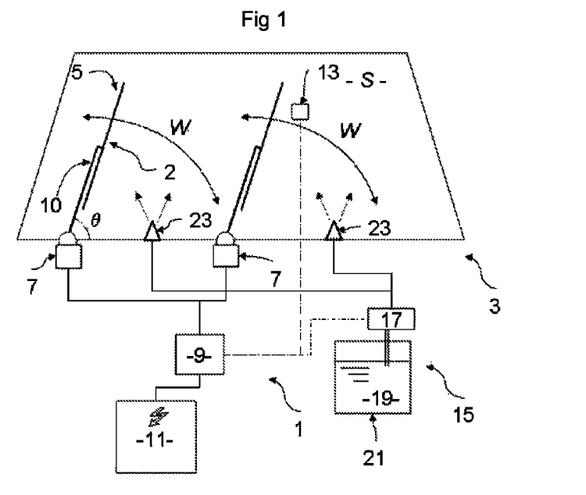
FIG. 1 is a schematic view of a windshield wiper unit.

The invention relates to a vehicle windshield wiper unit 1, and more particularly to a method to assess the wear of a wiper blade 5 in such a windshield wiper unit 1. FIG. 1 represents schematically a windshield 3 and the associated windshield wiper unit 1. The windshield wiper unit 1 comprises at least one wiping assembly 2, at least one motor 7 and one controller 9.

The windshield 3 comprises an external windshield surface S which receives rain or other stain from the surroundings when the vehicle is driven.

On said windshield surface S is placed at least one windshield wiping assembly 2. The at least one wiping assembly 2 comprises at least one wiper blade 5 made of rubber and held by respective wiper arms 10 connected to respective motors 7. In this example, only the wiper blades 5 are in contact with the windshield surface S.

The wiper unit 1 is usually controlled by a user via a lever or any form of actuator. Such an actuator may be in the passenger compartment, most often near the steering wheel or on the dashboard. The wiper unit 1 may also be controlled automatically by a rain sensor 13.

The rain sensor 13 is usually an optical sensor placed on the windshield surface S using infrared dispersion and reflection of infrared beams inside the windshield 3 glass.

Several wiping speeds W or programs are available: off, single wipe, intermittent INT, low speed LS and high speed HS. To supply the power to motors 7, the controller 9 can use pulse width modulation on the current delivered to said motors 7.

Motors 7 are able to set the wiping assemblies 2 in motion by applying a torque at the base of the wiping assemblies 2. Said motors 7 are fed with electrical power via the controller 9, configured to apply specific wiping programs by controlling the wiping speed W of the wiping assemblies 2. The power to run motors 7 is delivered by the vehicle battery 11 or an alternator of the vehicle.

When the wiping assemblies 2 are in motion, a friction arises between the wiper blades 5 and the windshield surface S. This friction is characterized by a friction coefficient B between the wiper blades 5 and the windshield surface S. The controller 9 is configured to derive said friction coefficient B.

The controller 9 is also configured to estimate the wear state of the wiper blades 5 by comparing the derived friction coefficient B to predetermined threshold values. These threshold values can either be preset in the controller 9 memory or calibrated every time a new set of wiper blades 5 is set up or every time the electronics of the vehicle is initiated. In the latter case, the controller 9 is configured to perform the calibration.

The controller 9 is also configured to generate an alert signal to inform the driver when the wiper blades are worn. For example the controller 9 may display a signal on the dashboard of the car.

The controller 9 is also configured to store the derived friction coefficient B data in its memory. This data can be transferred on demand for example to a diagnostic tool to state on wiper blades 5 wear, and allow preventive maintenance with quantitative measurements.

The controller 9 may also store other data such as data relative to speed of the car or ambient temperature.

The controller 9 may also be connected to the rain sensor 13.

The windshield wiper unit 1 may also comprise a windshield washing unit 15, which is also represented on FIG. 1. Said windshield washing unit 15 comprises a pump 17, connected to the controller 9, and configured to pump on driver request washing fluid 19 from a tank 21 to spraying nozzles 23. Said nozzles 23 project directly a washing fluid spray on the windshield surface S to clear it from dust or stain.

The invention also relates to a method to estimate the wear state of the wiper blades 5 of the wiper unit 1.

The motor applies a torque to the wiping assemblies 2 that are set in motion. This torque is function of a current supplied to motors 7. The friction of the rubber wiper blades 5 on the windshield surface S produces a friction torque opposed to the motor applied torque. The friction torque value increases with the wiping speed W.

A friction coefficient B can be associated to the friction torque. Said friction coefficient B is representative of the friction between the wiper blades 5 and the windshield surface S.

The friction torque also greatly depends on the wetness state of the windshield surface S. In particular, it is significantly lower when windshield surface S is wet. This is represented on FIG. 2, where the curves of the power consumption P of motors 7 as a function of wiping speed W are pictured. The wet power consumption P with a wet windshield surface S is represented by a first curve $P_{wet}$, and the power consumption P with a dry windshield surface S is represented by a second curve $P_{dry}$.

Figure 2:
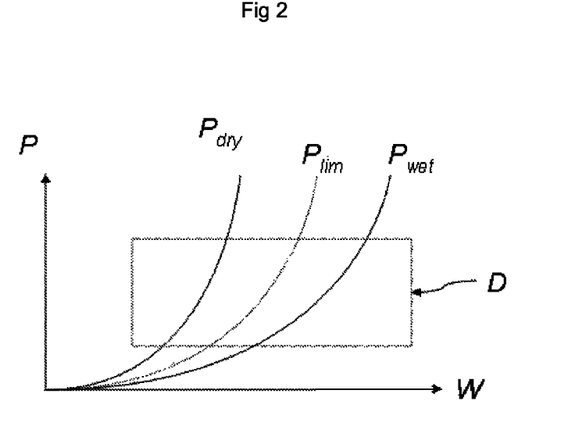
FIG. 2 is a simplified graph representing the power consumption as a function of the wiping speed in different windshield wetness state.

The different operating modes restrain the functioning domain to domain D, where the difference between wet and dry is easily done since the first curve $P_{wet}$ and the second curve $P_{dry}$ are easily distinguishable.

The power consumption P increases with wiping speed W. This dependency is not linear, and the power consumption P increases roughly with square or cube of the wiping speed W depending on friction model. But at any wiping speed W, the wet power consumption $P_{wet}$ when the windshield surface S is wet, is lower than the dry power consumption $P_{dry}$ when the windshield surface S is dry.

This allows drawing an intermediate power consumption curve $P_{lim}$. Below the intermediate power consumption curve $P_{lim}$ the windshield surface S is assumed wet, and above the intermediate power consumption curve $P_{lim}$ the windshield surface S is assumed dry.

The steepness of the power over speed curves P(W) depends on the friction coefficient B. The friction coefficient B can be of the form $P(W) \cdot W^{-\beta}$, where $\beta$ is a positive coefficient depending on the model chosen to represent the dynamics. In particular, the choice of $\beta=0$ corresponds to a direct comparison of the power values.

Using the Coulomb law, a factor of four to five is measured between friction on dry surface and friction on wet surface. The difference is therefore easily noticeable. For example the usual wet friction coefficient values on wet surface are around 0.2 or 0.3, whereas on dry surface, the usual dry friction coefficient value is above 0.8.

Figure 3:
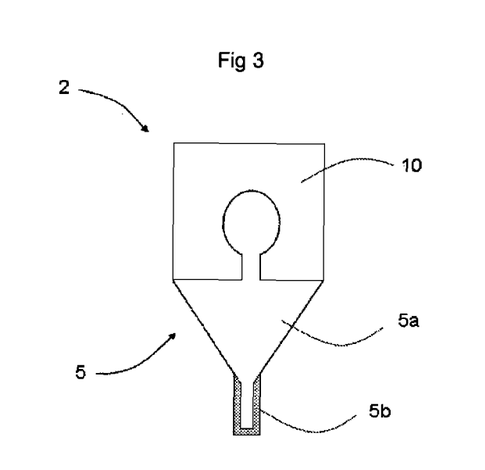
FIG. 3 is a schematic cross sectional view of a wiper blade.

The friction torque also depends on the wear state of the wiper blades 5. Referring to FIG. 3, wiping assemblies 2 usually comprise rubber wiper blades 5 supported by wiper arms 10. The rubber wiper blades 5 usually have a core 5a made of rubber partially coated with a coating layer 5b.

The surface of the core 5a may be hardened thanks to a chemical halogen treatment. The rubber core 5a has a high friction coefficient B with the dry windshield surface S which makes it likely to cling to the windshield surface S. To achieve more efficient wiping, a well known solution is to coat the surface of the core 5a with a coating layer 5b having a low friction coefficient B.

However, the coating layer 5b degrades with use and with environmental stresses such as ultra violet light and temperature. As the coating layer 5b wears off, the friction coefficient B between the wiper blades 5 and the windshield surface S increases when the windshield surface S is dry.

Experience shows that the friction coefficient B value on wet surface is relatively independent from the wear state of the wiper blades 5, and remains at the same value throughout the wiper blades 5 lifetime.

Consequently, it is possible to use the over time evolution of the friction coefficient B between the rubber wiper blades 5 and the dry windshield surface S as a reliable indicator of the wiper blades 5 wear.

Figure 4A:
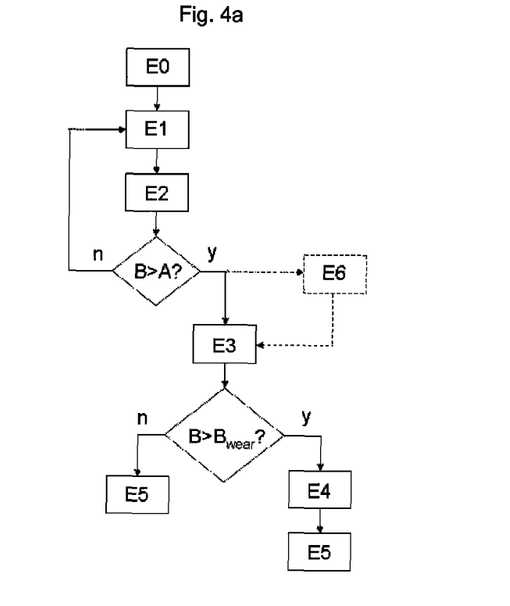
FIG. 4a is a flow chart showing the steps of the wear estimation method according to a first embodiment and a second embodiment of the invention.
Figure 5A:
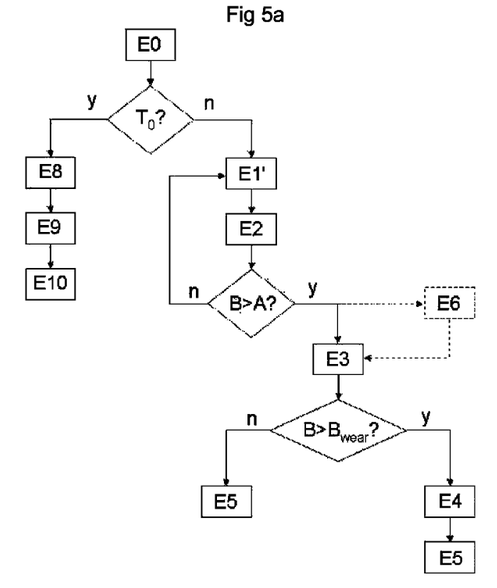
FIG. 5a is a flow chart showing the steps of the wear estimation method according to a third embodiment and a the fourth embodiment of the invention.

For better clarity, the steps of the wear estimation method are summarized hereafter, and are explained in details later in the description. The steps of the wear estimation method are illustrated in FIGS. 4a and 5a. These FIGS. 4a and 5a correspond to different embodiments of the wear estimation method.

E0: setting the wiper blades 5 in motion,
E1, E1': deriving the friction coefficient B,
E2: comparing the derived friction B with a first predetermined threshold value A,
E3: comparing the derived friction B with a second predetermined threshold value $B_{wear}$,
E4: storing derived friction B data
E5: informing user
E6: stopping wiping motion—optional

1. FIRST EMBODIMENT

Figure 4B:
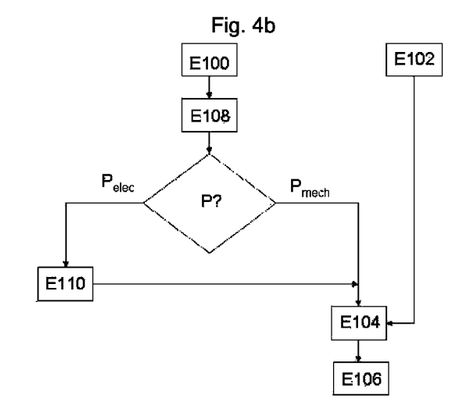
FIG. 4b is a flow chart showing the substeps of one step of the wear estimation method according to the first embodiment and the second embodiment of the invention.

FIGS. 4a and 4b

FIG. 4a represents the steps of the wear estimation method according to the first embodiment.

Step E0 of Setting the Wiper Blades 5 in Motion

The wiper blades 5 can be set in motion by the user, or they can be automatically set in motion after detection of rain by the rain sensor 13.

Step E1 of Deriving the Friction Coefficient B (FIG. 4b)

To estimate the wear of the wiper blade, a first step E1 consists in deriving the friction coefficient B between the wiper blades 5 and the windshield surface S.

According to the first embodiment, step E1 comprises a plurality of sub steps among which:

E100: measuring the power consumption P,
E102: measuring the wiping speed W,
E104: determining the power consumption, wiping speed P,W operating point,
E106: deriving the friction coefficient B,
E108: dividing the power consumption P or the derived friction coefficient B by a size factor,
E110: converting power (optional)

In a first substep E100, the electric power consumption $P_{elec}$ of motors 7 is measured.

The controller 9 comprises means to measure the electrical power consumption $P_{elec}$ of motors 7. For example, said consumption measuring means can comprise a current estimator measuring the current delivered to motors 7. The current estimator is, for example, based on parameters of the electrical circuit such as the tension applied at motors 7, the speed to voltage coefficient of motors 7, the measured speed of motors 7, the resistance of motors 7 and the inductance of motors 7.

The current can also be directly measured by a current measurement apparatus such as shunt, current sensor or current mirrors.

The estimated current is then multiplied by the voltage applied to motors 7 to obtain the instantaneous power. An integrator is used to obtain a mean power value over one, preferably few cycles. The effect of the integration is to remove the variation of power consumption due to aerodynamic. Then, the mean electrical power consumption is divided by the time necessary to accomplish one wiping cycle to obtain the electrical power consumption $P_{elec}$.

In general, a factor influencing the power consumption P, either electrical power or mechanical power, of motors 7 is the size factor of the wiper unit 1. The size factor of the wiper unit 1 may comprise: the wiper arm 10 length, the wiper blade 5 length and the wiping angle θ. Hence, the power consumption P of motors 7 is relative to the wiper unit 1 in use, and differs for vehicles with different size factor wiper unit 1. As a consequence, the power consumption P of wiper units 1 having different size factors are not comparable. Likewise the derived friction coefficients B of wiper units 1 having different size factors are not comparable, since the friction coefficients B are derived from the power consumption P.

As mentioned before, the wear estimation method involves comparing the derived friction coefficient B from the vehicle wiper unit 1 to a predetermined reference threshold. This implies calculating a predetermined reference threshold for every size factor wiper unit 1. Given the great number of available size factor wiper unit 1, this results in a time consuming process.

A solution to overcome this drawback is to divide the electrical power consumption $P_{elec}$ of motors 7 by the size factor of the wiper unit 1 during a substep E108. If there is a plurality of wiper blades 5, the size factor is the sum of the size factors of the plurality of wiper blades 5. The power consumption $P_{elec}$ of the wiper unit 1 thus obtained is not relative to the wiper unit 1 size factor. It is the absolute electrical power consumption $P_{elec}$. This absolute electrical power consumption $P_{elec}$ can be compared with absolute electrical power consumption $P_{elec}$ of different size factor wiper unit 1. It is particularly interesting as the same predetermined threshold values can be preset in the controller 9 of vehicles with different size wiper unit 1.

During the substep E100, the controller 9 measured the electrical power consumption $P_{elec}$, however, to determine a power consumption, wiping speed P,W operating point, it is needed to calculate the actual power consumption of motors 7, i.e., the mechanical power consumption $P_{mech}$.

During the step E110, the controller multiplies the electrical power consumption $P_{elec}$ by an electrical efficiency coefficient.

The electrical efficiency coefficient represents the efficiency of an electrical circuit to transform the electrical power into mechanical power. The electrical efficiency coefficient depends, for example, on the electrical circuit hardware and on the wetness of the windshield surface S. It may range from 40% to 80%. For example, it has a higher value when the windshield is wet. The variation of the electrical efficiency coefficient according to wetness state may be determined experimentally and its value according to meteorological condition can be preset. To take in account said variation of the electrical efficiency coefficient, the controller 9 multiplies the absolute electrical power consumption $P_{elec}$ by the electrical efficiency coefficient value corresponding to the current wetness state of the windshield surface S.

During a substep E102, the controller determines the wiping speed of blades 5, for example by knowing the wiping speed W corresponding to the current wiping mode: off, intermittent INT, low speed LS, or high speed HS.

During a substep E104, the controller 9 determines a mechanical power consumption, wiping speed P,W operating point for the wiper unit 1. In the current embodiment, it is the absolute mechanical power consumption, wiping speed operating point P,W.

During the last substep E106, the controller derives a friction coefficient B from the absolute mechanical power consumption, wiping speed operating point P, W and a friction model preset in the controller 9 memory. Since the friction coefficient B is derived from the absolute mechanical power consumption $P_{mech}$, it is not relative to the size factor of the wiper unit 1. It can be called absolute derived friction coefficient B.

It is also possible to perform the substep E108 of dividing by the size factor of the wiping unit 1, after the substep E106 of deriving the friction coefficient B instead of after substep E100 of measuring the electrical power consumption $P_{elec}$.

Step E2 of Determining the Wetness State of the Windshield Surface S

During a step E2 (FIG. 4a), the absolute derived friction coefficient B is compared to an absolute first predetermined threshold value A to determine the wetness state of the windshield surface S.

The absolute first predetermined threshold value A is representative of a predetermined dry-state friction. It is represented by a dotted line "A" on FIG. 6. If the absolute derived friction coefficient is equal or greater than the absolute first predetermined threshold value A, it signified that the windshield surface S is dry. Otherwise, the windshield surface S is wet.

Figure 6:
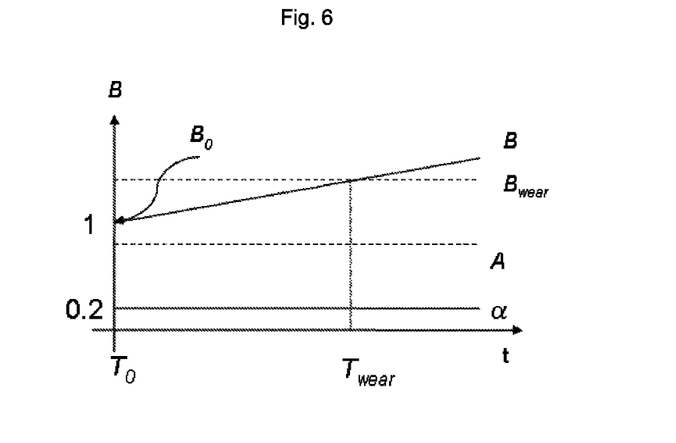
FIG. 6 is a graph representing the friction coefficient of a wiper blade over time.

Said absolute first predetermined threshold value A may be determined experimentally by the manufacturer for example, by performing friction measurements on a test windshield wiper unit.

For example, the test windshield wiper unit may comprise elements similar to the windshield wiper unit 1 of an actual vehicle, such as test wiper blades held by test wiper arms, activated by test motors consuming a power. Also similarly to the windshield wiper unit 1 of an actual vehicle, the test wiper blades may wipe the test windshield surface over a wiping angle, at a wiping speed.

The size factor of the test unit can be measured experimentally.

The determination of the absolute first predetermined threshold value A would comprise the steps of wetting the test windshield surface using and running a certain number of cycles while measuring the power consumption and determining the wiping speed.

The power consumption would be divided by the size factor of the test wiping unit in order to obtain the absolute power consumption of the motor.

The absolute power consumption and the wiping speed would then be used to obtain an absolute reference wet friction coefficient value α. Said absolute reference wet coefficient value is represented by the plain horizontal curve a on FIG. 6.

The absolute first predetermined threshold value A above which the test windshield surface is considered dry will be determined, for example, by setting it to at least four times of said reference wet friction coefficient value α.

The absolute first predetermined threshold value A may then be stored in the controller 9 memory of the actual vehicle. The absolute second predetermined threshold $B_{wear}$ value can be used for wiper units 1 having different size factors.

As described in substep E108, it is possible to divide the derived friction coefficients by the size factor of the test wiping unit instead of dividing the power consumption.

Step E3 of Estimating the Wear State of the Wiper Blades 5

The step E3 comprises the comparison of the absolute derived friction coefficient B to an absolute second predetermined threshold value $B_{wear}$ above which the wiper blades 5 are considered as worn.

As long as the absolute derived friction coefficient B remains below the absolute second predetermined threshold value $B_{wear}$, the wiper blades 5 are adapted to wipe. The wear state is detected when the absolute derived friction coefficient B is equal or greater than the absolute second predetermined threshold value $B_{wear}$. The moment when the absolute derived friction coefficient B is equal to the absolute second predetermined threshold value $B_{wear}$ is referred to as wear detection time $T_{wear}$.

The absolute second predetermined threshold value $B_{wear}$ may be a memorized value chosen according to reference friction coefficient values on dry surfaces.

For example the absolute second predetermined threshold value $B_{wear}$ may be determined experimentally by the manufacturer by performing friction measurements on the test wiper unit previously described.

The determination of the absolute second predetermined threshold value $B_{wear}$ would comprise the step of measuring the power consumption of the test motor on the dry test windshield surface.

The measured power consumption would then be divided by the size factor of the test wiping unit. Thus the absolute power consumption would be obtained.

The wiping speed of the test wiper blades would be determined.

The absolute power consumption and wiping speed would be used to derive the absolute friction coefficient between the test wiper blades and the test windshield surface.

The evolution over time of the absolute derive friction coefficient would be monitored over time along with the wiping performance of the test wiper blades. For example the wiping performance becomes unacceptable when the test windshield surface is still wet or stained after wiping. The absolute derive friction coefficient corresponding to an unacceptable wiping performance, would be set as the absolute second predetermined threshold value $B_{wear}$.

Another possibility to estimate the wear state of the wiper blades 5 is to store the absolute derived friction coefficient B obtained with a new wiper blade 5 and to divide subsequent measurements of the absolute derived friction coefficient B by its stored value. A wear coefficient is thus obtained.

The initial value of the wear coefficient is 1. The wear coefficient will then increase according to the wear state of the wiper blade 5. A threshold value of the wear coefficient is set, for example to 1.5 times its initial value. Hence, a 50% increase of the absolute derived friction coefficient B leads to the wiper blade 5 being estimated as worn.

As described in substep E108, it is possible to divide the derived friction coefficients by the size factor of the test wiping unit instead of the power consumption.

Step E4 of Storing and Restoring Data

If the absolute derived friction coefficient B is lower than the second predetermined threshold value $B_{wear}$, the wiping performance provided by the wiper blades 5 is acceptable. In this case, the controller 9 is configured to store the data acquired over a wiping period. The wiping period may, for example, run from the moment when the wiper blades 5 are set in motion until the wiper blades 5 are stopped.

For example, the controller 9 is configured to store the highest absolute derived friction coefficient B or absolute power consumption P values acquired over the wiping period.

The controller 9 may restore on demand the stored data for example to a diagnostic tool. The data includes for example data concerning the wear estimation. It can also store other data related to the vehicle state, for example mileage, speed, ambient temperature. This data can allow preventive maintenance with quantitative measurements.

Step E5 of Generating an Alert Signal

Upon detection of wear state of the wiper blades 5, the controller 9 generates a signal about the wear state of the wiper blades 5. For example, an indicator may be lit on the dashboard to invite the user to proceed to a wiper blades 5 renewal.

The step E4 of storing and restoring data can be performed after detection of wear state of the wiper blades 5. This makes it possible for the controller 9 to adapt the wiping speed W as a function of the evolution of the absolute derived friction coefficient B.

Step E6 of Stopping Wiping Motion

The wear estimation method can further comprise an optional step E6 of stopping the wiping motion of the wiper blade 2 when the windshield surface S is dry. Step E6 can be performed after step E2 of determining the wetness state of the windshield surface S. Step E6 is represented by a dotted rectangle on FIG. 4a.

This allows avoiding unnecessary use and hence early wear of the wiper blades 5. It also allows avoiding unnecessary power consumption.

2. SECOND EMBODIMENT

The difference between the second embodiment and the previously described embodiment is that the controller 9 directly measures the mechanical power consumption $P_{mech}$ of motors 7 instead of their electrical power consumption $P_{elec}$.

FIG. 4a represents the steps of the wear estimation method according to the second embodiment.

Step E1 of Deriving the Friction Coefficient B

During a substep E100 (FIG. 4b), the controller 9 measures the mechanical power consumption $P_{mech}$ of motors 7. In this case, the controller 9 comprises means, to measure the torque from motors 7 such as a torque estimator. It also comprises means to estimate the motors 7 speed. The controller 9 also comprises an integrator to obtain a mean torque value over one, preferably few cycles. The following analogy can be made with respect to the electrical power consumption $P_{elec}$: mechanical power is analog to electrical power, torque is analog to current and motor speed is analog to voltage.

With this method the electrical efficient coefficient needs not to be estimated as the mechanical power consumption $P_{mech}$ is directly measured. The mechanical power consumption $P_{mech}$ is used to determine the power consumption, wiping speed operating point P,W.

Similarly to the first embodiment, the substep E108 of dividing by the size factor of the wiper unit 1 is performed. Thus the absolute mechanical power consumption $P_{mech}$ is obtained. The substep E108 of dividing by the size factor of the wiper unit 1 can be performed either after the substep E100 of measuring the mechanical power consumption $P_{mech}$, or after the substep E106 of deriving the friction coefficient B. Likewise, the derived friction coefficient B is the absolute derived friction coefficient B.

The substep E104 of determining the power consumption, wiping speed operating point P,W is performed similarly to the first embodiment.

Similarly to the first embodiment, the second embodiment comprises the step E0 of setting the wiper blades 5 in motion, the step E1 of deriving the absolute friction coefficient B, the step E2 of comparing the absolute derived friction coefficient B with the first predetermined threshold value A, the step E3 of comparing the absolute derived friction coefficient B with the absolute second predetermined threshold value $B_{wear}$, the step E4 of storing data, the step E5 of informing the user, the step E6 of stopping wiping motion.

3. THIRD EMBODIMENT

Figure 5B:
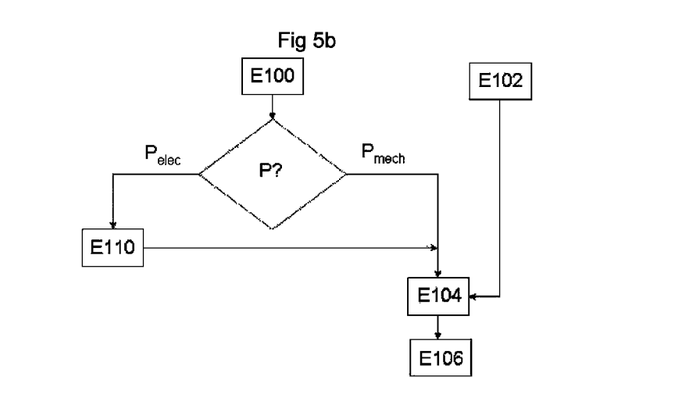
FIG. 5b is a flow chart showing the substeps of one step of the wear estimation method according to the third embodiment and fourth embodiment of the invention.

FIGS. 5a, 5b and 6

The difference between the third embodiment and the first embodiment is that the step E1' of deriving the friction coefficient B, does not comprise the substep E108 of dividing the power consumption P or the derived friction coefficient B by the size factor of the wiping unit 1. FIG. 5a represents the steps of the wear estimation method according to the third embodiment.

Similarly to the first embodiment, the step E1' of deriving the friction coefficient B of the third embodiment comprises the substeps: E100 of measuring the electrical power consumption $P_{elec}$, E110 of converting the measured electrical power consumption $P_{elec}$ into mechanical power consumption $P_{mech}$, E102 of measuring the wiping speed, E104 of determining the power consumption, wiping speed operating point P,W, and E106 of deriving the friction coefficient B (see FIG. 5b).

However, this time the power consumption P is not divided by the size factor of the wiping unit 1. Hence the power consumption P is relative to the size factor of the wiping unit 1. It may be called it relative power consumption P.

Likewise, the derived friction coefficient B is not divided by the size factor of the wiping unit 1. Hence the derived friction coefficient B is relative to the size of the wiping unit 1 of the vehicle. It may be called relative derived friction coefficient B.

The first and second predetermined threshold values A, $B_{wear}$ have to be relative to each size factor of wiper unit 1. They may be called relative first predetermined threshold value A and relative second predetermined threshold value $B_{wear}$.

Step E8 of Determining the Relative First Predetermined Threshold Value A

There are several solutions to determine the relative first predetermined threshold value A.

According to a first solution illustrated on FIG. 5a, the controller 9 may perform a calibration of the wiper unit 1. The calibration would be performed when changing the wiper blades 5 or at initiation/reset of the vehicle electronics. This moment of changing the wiper blades 5 or initiating/resetting the vehicle electronics is illustrated on FIG. 6 and referred to as the initial moment $T_0$.

The calibration would comprise steps similar to the ones performed to determined the absolute first threshold value A. Except in this case the calibration steps are performed on the actual vehicle wiper unit 1, not on a test wiper unit.

The calibration would comprise a steps of wetting the windshield surface S using windshield washer unit 15 if the vehicle is equipped, and running a certain number of cycles while measuring the relative electric power consumption $P_{elec}$ to obtain a relative reference wet coefficient value α. Similarly to the determination of the absolute threshold values, FIG. 6 may represent the relative threshold values. Said relative reference wet coefficient value is represented by the plain horizontal curve α.

The relative first predetermined threshold value A above which the windshield surface S is considered dry will be deduced, for example, by setting it at least four times of said wet windshield surface S reference wet coefficient value α, in reference of Coulomb law of friction.

According to a second solution, the relative first predetermined threshold value A would be determined experimentally by the manufacturer with a test wiping unit and preset in the controller memory. The steps to determine the relative first predetermined threshold value A would be mostly similar to the steps performed for the determination of the absolute first predetermined threshold value A. The difference would be that the step of dividing by the size factor of the test wiping unit would not be performed. As a consequence, the relative first predetermined threshold value A can only be used for vehicle having the same size factor as the test wiping unit.

According to a third solution, the controller 9 may also store and compare the power consumption or friction coefficient values over a predetermined amount of time, and use lowest values for wet reference, and highest values for dry reference.

Step E9 of Determining the Relative Second Predetermined Threshold Value $B_{wear}$ Similarly to the determination of the relative first predetermined threshold value A, there exist several possibilities to determine the relative second predetermined threshold value $B_{wear}$.

According to a first solution, a calibration of the relative second predetermined threshold value $B_{wear}$ would be performed at the initial moment $T_0$. The controller 9 may run a predetermined number of wiping cycles on the windshield surface S.

The relative electric power consumption $P_{elec}$ is measured and converted in relative mechanical power consumption $P_{mech}$ as described earlier. The wiping speed W is measured as described earlier. A relative mechanical power consumption, wiping speed operating point P,W is determined from the measured relative mechanical power consumption $P_{mech}$ and the wiping speed W.

From this relative mechanical power consumption/wiping speed operating point P/W, a reference friction coefficient $B_0$ of the dry windshield surface S is determined.

Said reference friction coefficient $B_0$ is used to determine the relative second predetermined threshold value $B_{wear}$. For example, the controller 9 may set the second predetermined threshold value $B_{wear}$ as a multiple of the value of the reference friction coefficient $B_0$.

According to a second solution, the relative second predetermined threshold value $B_{wear}$ would be determined experimentally by the manufacturer for example with a test wiping unit, and preset in the controller 9 memory. This relative second predetermined threshold value $B_{wear}$ can only be used for vehicle having the same size factor as the test wiping unit.

Step E10 of Storing the Relative First Predetermined Threshold Value A and the Relative Second Predetermined Threshold Value $B_{wear}$ After calculating the relative first predetermined threshold value A and the relative second predetermined threshold value $B_{wear}$, the controller 9 stores them for future reference in the comparison with the relative derived friction B.

The steps E8 of determining the relative first predetermined threshold value A, E9 of determining the relative second predetermined threshold value $B_{wear}$ and E10 of storing the relative first predetermined threshold value A and the relative second predetermined threshold value $B_{wear}$ have to be performed every time a new set of wiper blade 5 is set and/or every time the electronics of the vehicle is initiated.

4. FOURTH EMBODIMENT

The difference between the fourth embodiment and the third embodiment is that the controller 9 directly measures the mechanical power consumption $P_{mech}$ of motors 7 instead of their electrical power consumption $P_{elec}$ as described in the second embodiment.

FIG. 5a represents the steps of the wear estimation method according to the fourth embodiment.

The steps E0, E1', E2, E3, E4, E5, E6, E8, E9 and E10 are performed similarly to the third embodiment of the invention.

The method of wear state estimation relies on measures that imply the whole of the windshield surface S that is wiped during a cycle, which is more reliable than the usual optical sensor 13, and the counting of the number of wipe cycles. The method also does not involve adding complex hardware to the wiping unit 1.

The method also offers a possibility to use the same reference values for all vehicles instead of having to perform a calibration of the windshield unit 1 every time a new wiper blade 5 is set up.

The invention claimed is:

1. A method to estimate the wear state of wiper blades of a vehicle windshield wiper unit, said windshield wiper unit comprising:
at least one wiper blade configured to wipe a windshield surface when activated,
at least one motor configured to activate the at least one wiper blade at a wiping speed, and
a controller configured to control the at least one motor, said method comprising:
deriving a friction coefficient between the at least one wiper blade and the windshield surface;
comparing the derived friction coefficient to a first predetermined threshold value, to determine the wetness of the windshield surface; and
when the windshield surface is dry, comparing the derived friction coefficient to a second predetermined threshold value to estimate the wear state of the at least one wiper blade.

2. The method as claimed in claim 1, wherein the at least one motor has a power consumption, said method further comprising dividing the power consumption by a size factor of the windshield wiping unit.

3. The method as claimed in claim 1, the method further comprising dividing the derived friction coefficient by the size factor of the windshield wiping unit.

4. The method as claimed in claim 2, the windshield wiping unit wiping the windshield surface at a wipe angle and comprising at least one wiper arm, and at least one wiper blade, wherein said windshield wiping unit presents a size factor comprising the wipe angle, the length of the at least one wiper arm and the length of the at least one wiper blade.

5. The method as claimed in claim 2, the method further comprising determining the first predetermined threshold value with a test windshield wiping unit, said determination comprising:
wetting the test windshield surface,
measuring the power consumption of the at least one test motor,
determining the wiping speed of the at least one test wiper blade,
using the measured power consumption and wiping speed to deduce a reference wet friction coefficient of the wet windshield surface,
using the reference wet friction coefficient to determine the first predetermined threshold value,
said determination further comprising a step of dividing the power consumption or the first predetermined threshold value by the size factor of the test wiper unit.

6. The method as claimed in claim 2, further comprising determining the second predetermined threshold value with the test windshield wiping unit, said determination comprising:
measuring the power consumption of the at least one test motor on dry test windshield surface,
determining the wiping speed of the at least one test wiper blade on dry test windshield surface,
using the measured power consumption and determined wiping speed to derive the friction coefficient,
monitoring the over time wiping performance and the corresponding friction coefficient to determine the second predetermined threshold value,
said determination further comprising a step of dividing the power consumption or the friction coefficient by the size factor of the test wiping unit.

7. The method as claimed in claim 1, the controller being connected to a windshield washing unit, wherein the first predetermined threshold value is determined using a calibration, the calibration comprising:
wetting the windshield surface by activating the windshield washing unit,
measuring the power consumption of the at least one motor during a certain number of cycles done by the at least one wiper blade,
using the measured power consumption to deduce a reference wet friction coefficient of the wet windshield surface,
using the reference wet friction coefficient to determine the first predetermined threshold value.

8. The method as claimed in claim 7, wherein the first predetermined threshold value is a multiple of the reference wet friction coefficient, at least four times the reference wet friction coefficient.

9. The method as claimed in claim 1, wherein the second predetermined threshold value, is determined using a calibration, the calibration comprising:
measuring the power consumption of the at least one motor on dry windshield surface,
determining the wiping speed of the at least one wiper blade on dry windshield surface,
using the measured power consumption and determined wiping speed to derive an initial dry friction coefficient of the dry windshield surface,
using said initial dry friction coefficient to determine the second predetermined threshold value.

10. The method as claimed in claim 9, wherein the second predetermined threshold value is a multiple of said corresponding friction coefficient or said initial dry friction coefficient.

11. The method as claimed in claim 1, further comprising generating a signal when the at least one wiper blade is estimated worn.

12. The method as claimed in claim 1, further comprising storing the derived friction coefficient values and restoring them.

13. A windshield wiper unit comprising:
- at least one wiper blade configured to wipe a windshield surface when activated;
- at least one motor configured to activate the at least one wiper blade; and
- a controller configured to:
- control the at least one motor,
- derive a friction coefficient between the at least one wiper blade and the windshield surface,
- compare the derived friction coefficient to a first predetermined threshold value, to determine the wetness of the windshield surface, and
- if the windshield surface is dry, compare the derived friction coefficient to a second predetermined threshold value, in order to estimate the wear state of the at least one wiper blade.

14. The windshield wiper unit as claimed in claim 13, wherein the controller comprises means for performing a calibration of the first predetermined threshold value and of the second predetermined threshold value.

15. The windshield wiper unit as claimed in claim 13, wherein the controller comprises means to generate an alert signal when the at least one wiper blade is estimated worn.

16. The windshield wiper unit as claimed in claim 13, wherein the controller comprises means for storing the values of the derived friction coefficient and restoring them.

* * * * *

UNITED STATES PATENT AND TRADEMARK OFFICE
CERTIFICATE OF CORRECTION

PATENT NO. : 9,539,984 B2  
APPLICATION NO. : 14/118750  
DATED : January 10, 2017  
INVENTOR(S) : Dominique Dias Page 1 of 1

It is certified that error appears in the above-identified patent and that said Letters Patent is hereby corrected as shown below:

On the Title Page

Under item (65) Prior Publication Data, Line 2, insert item (30) Foreign Application Priority Data:

-- (30) Foreign Application Priority Data  
May 20, 2011 (EP) 11305619.6 --.

Signed and Sealed this  
Third Day of April, 2018

Andrei Iancu  
*Director of the United States Patent and Trademark Office*